United States Patent [19]

Weissman

[11] Patent Number: 4,708,655

[45] Date of Patent: Nov. 24, 1987

[54] CONTOURED DENTAL POST AND DRILL JIG FOR USE THEREWITH

[76] Inventor: Bernard Weissman, 225 E. 48th St., New York, N.Y. 10017

[21] Appl. No.: 884,221

[22] Filed: Jul. 10, 1986

Related U.S. Application Data

[63] Continuation-in-part of Ser. No. 735,548, May 20, 1985, Pat. No. 4,600,392.

[51] Int. Cl.⁴ .............................................. A61C 5/04
[52] U.S. Cl. .................................................... 433/225
[58] Field of Search ...................... 411/439, 429, 452; 433/221, 220, 225, 173, 174; 168/23

[56] References Cited

U.S. PATENT DOCUMENTS 1,139,028  5/1915  Gibson ................................ 433/221
4,097,168  6/1978  Pagel .................................. 411/452

Primary Examiner—Robert Peshock
Attorney, Agent, or Firm—Goodman & Teitelbaum

[57] ABSTRACT

A contoured dental post for retaining a dental restoration on a prepared tooth stub, the dental post including an elongated cylindrical body portion having peripheral grooves for anchoring the body portion within a cement prepared bore in the tooth stub. A pair of radially projecting ribs angularly extends downwardly along a portion of the length of the body portion on opposite sides of the body portions. The ribs project laterally to approximate the oval shape of the canal in the tooth stub into which the bore is formed, where the ribs taper downwardly to approximate the conical shape of the canal. One rib is longer than the other rib to provide a pilot for inserting the ribs into the bore. A drill jig is also provided for contouring the canal to receive the dental post. The drill jig includes a head block having a depending central shaft extending therefrom for insertion into the bore. At least one offset aperture is laterally positioned in the head block, the aperture having angular side walls. The aperture extends downwardly into a portion of the shaft along an angular penetration into the shaft. The drill jig is utilized to form a pair of angular lateral apertures along a preformed central bore in the tooth stub to accommodate the ribs on the dental post for suitable accommodation of the dental post into the tooth stub. The drill jig can be provided with a second offset aperture or with a fin on the shaft.

17 Claims, 21 Drawing Figures

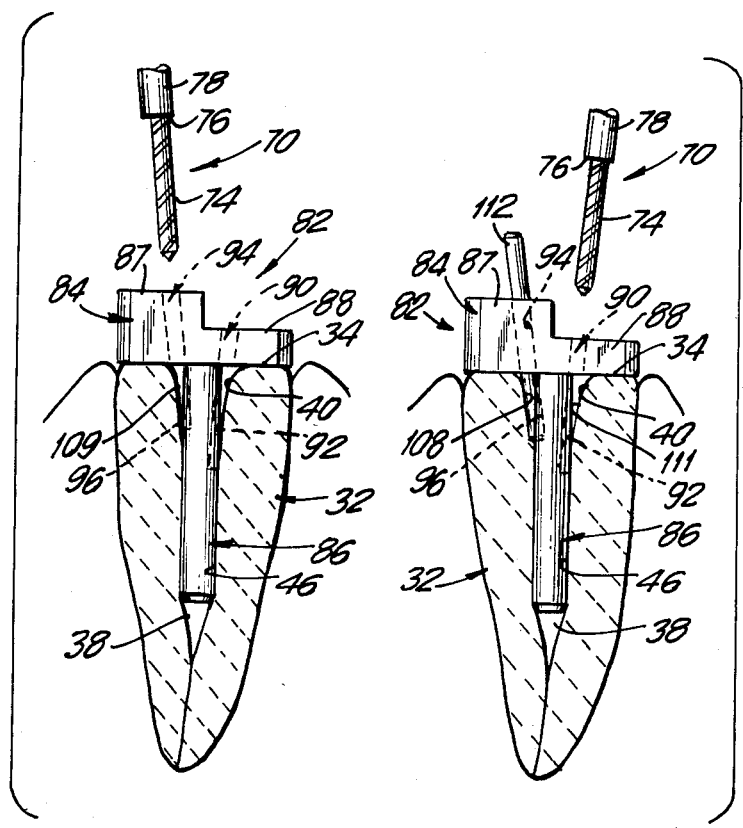
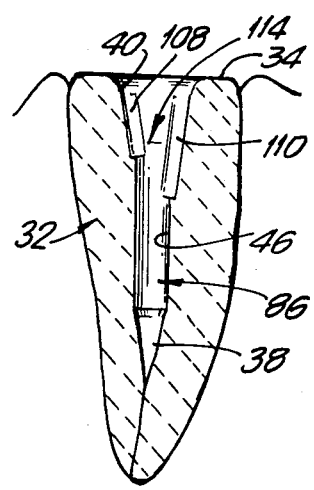
FIG.12  FIG.13  FIG.14
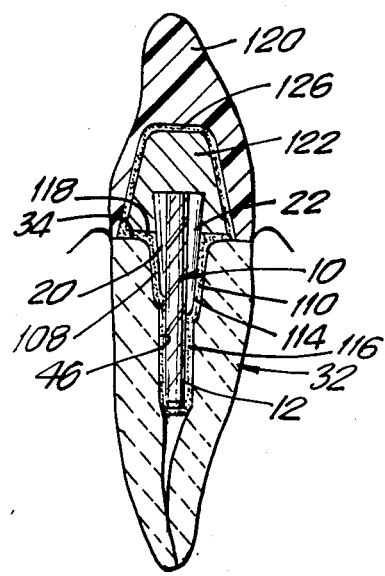
FIG.15

CONTOURED DENTAL POST AND DRILL JIG FOR USE THEREWITH

RELATIONSHIP TO OTHER APPLICATIONS

This Application is a Continuation-In-Part Application to co-pending U.S. patent application Ser. No. 735,548 filed on May 20, 1985, now U.S. Pat. No. 4,600,392 for a Contoured Dental Post.

BACKGROUND OF THE INVENTION

This invention relates to a dental post system for retaining a dental restoration onto a prepared tooth stub, and more particularly to a contoured dental post which more suitably accommodates the actual shape of the tooth canal in the tooth stub.

In the restoration of devitalized dentition, it is a well known practice to utilize a dental post for retaining a superstructure onto a tooth stub. Typically, the tooth stub is prepared by cutting down the damaged tooth to provide a suitable surface, and then drilling a desired depth into the apical canal to provide an enlarged bore for receiving the dental post. The dental post is then inserted and cemented in the bore. An appropriate core is provided or built up on an upper portion of the dental post, and dental restorative material is used to build a superstructure on the core.

Typically, dental posts heretofore utilized have a generally circular cross section. In preparing the tooth stub to receive such dental posts, circular drill bits are utilized to pre-drill the canal to form a circular bore. The dental posts are then inserted into these bores. However, the actual canal in the tooth stub does not have a circular shape, especially at the upper part thereof, where the canal tends to flare outwardly and often approaches an oval shape.

While it would be possible to drill the canal wide enough to encompass the flared upper portion in order to change the oval shape into a circular shape, this would tend to destroy healthy dentition and weaken the existing tooth stub. As a result, prior art practice has been to drill out the canal using only that size of drill bit which is adequate enough to receive the dental post. Cement was then inserted into those portions of the canal that were larger than the drilled bore so that the cement filled in the gaps between the inserted dental post and the existing canal shape.

The use of such cement to fill in the disparity between the post and the actual canal shape caused problems after the restoration was built up. The cement had a tendency to loosen, permitting the dental restoration to move with respect to the tooth stub. Such movement permits entry of contaminants and decay between the dental restoration and the tooth stub, and may even cause the dental post to be dislodged from the canal, thus requiring replacement of the restoration.

In the co-pending parent application there was provided a solution to this problem by providing a dental post having a contoured periphery to correspond with the oval shape at the mouth of the canal. The dental post included a pair of diametrically opposed, radially projecting ribs which extended longitudinally along at least a portion of the pin. The ribs were suitable to approximate the oval shape of the canal in the tooth stub.

While the ribs provided for such approximation to the oval shape in the width of the canal, the shape of the ribs had substantially longitudinal outer edges with a rather dramatic rounded lower edge. The actual shape at the upper part of the canal is not only oval in width, but is also conical in depth. Accordingly, the presence of the ribs were useful but still did not fully approximate the conical shape and excess healthy dentition had to be removed in order to accommodate the shape of the ribs.

SUMMARY OF THE INVENTION

Accordingly, it is an object of the present invention to provide a dental post which avoids the aforementioned problems of prior art dental posts.

Another object of the present invention is to provide a dental post with a contour which is better suited to approximate not only the actual oval shape of the canal's width, but also to closer approximation the depth of the canal.

Another object of the present invention is to provide to a dental post having a substantially cylindrical body portion with laterally extending contouring means which serve to contour the post both in the lateral and longitudinal directions to approximate the oval cross section and the tapered longitudinal section of a tooth canal.

A further object of the present invention is to provide a dental jig for use in providing a suitable contour shape to a bore in the tooth stub which approximates the tooth canal both in its planar cross section and its vertical cross section.

Briefly, in accordance with the present invention, there is provided a dental post for retaining a dental restoration onto a prepared tooth stub. The dental post includes a cylindrical body portion with appropriate anchoring means for securing the post within a prepared bore formed in the tooth stub. At least one downwardly tapered rib radially projects from the body portion. The rib extends longitudinally along at least a portion of the length of the body portion. The presence of the rib provides a somewhat oval cross sectional shape corresponding to the cross sectional oval shape of the canal in the tooth stub. It also provides a somewhat conically tapered vertical section which again approximates the conical shape of the canal in the tooth stub. Accordingly, a minimum amount of healthy dentition is removed in the formation of the bore.

In a preferred embodiment of the present invention, there is provided a pair of diametrically opposed radially projecting ribs, both of which are downwardly tapered. One of the ribs being shorter than the other.

The present invention also contemplates a dental drill jig for contouring a predrilled bore in the tooth stub to closely approximate the shape of the canal. Such contoured shape will then best accommodate the contoured pin previously described. The dental jig includes a head block from which depends an elongated shaft. The shaft can be inserted into the predrilled bore initially formed through the canal of the tooth stub. At least one offset aperture is provided in the drill jig. The offset aperture includes angled side walls which pass through the head block. The angled aperture continues along the shaft forming an angular aperture along at least a portion of the length of the shaft with the aperture in the shaft being opened.

The aforementioned objects, features and advantages of the present invention will, in part, be pointed out with particularity, and will, in part, become obvious from the following more detailed description of the present invention taken in conjunction with the accompanying drawings, which form an integral part thereof.

BRIEF DESCRIPTION OF THE DRAWINGS

In the drawings:

FIG. 12 shows a cross sectional view through the tooth stub similar to FIG. 3, showing the use of the dental drill jig of FIG. 9 in a second step in the formation of the contoured bore;

FIG. 13 is a view similar to that shown in FIG. 12, showing the use of the dental drill jig of FIG. 9 in a third step in the formation of the contoured bore;

FIG. 14 is a cross sectional view through the tooth stub, showing the contoured bore formed therein;

FIG. 15 is a perspective view through the tooth stub, showing insertion of the contoured dental post and the restoration provided on the tooth stub;

In the various figures of the drawings, like reference characters designate like parts.

DESCRIPTION OF THE PREFERRED EMBODIMENTS

Figure 1:
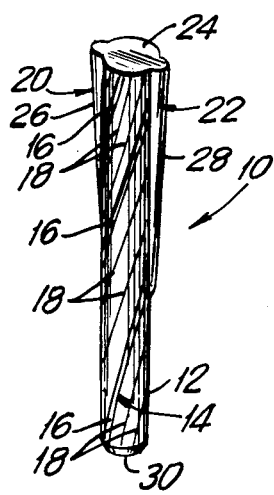
FIG. 1 is a perspective view of the contoured dental post in accordance with the present invention.

Referring now to FIG. 1, there is shown a dental post 10, according to the present invention, for insertion into a tooth stub upon which a dental restoration will be built up. The dental post 10 includes a substantially cylindrical body portion 12 provided with a plurality of helical grooves 14 for anchoring the dental post 10 in a cement prepared bore provided in the tooth stub.

The anchoring groove means can be of varying types. For example, they can be helical flutes of the type provided in U.S. Pat. No. 4,479,783, issued to the inventor of the present invention. These flutes are the helical grooves 14 shown in FIG. 1, and include a wider groove 16 separated by a pair of narrower grooves 18. The pitch of the grooves would be greater than the length of the post so as to terminate at the lower end of the post 10 before completing one revolution, thus providing also a vent for when the post 10 is inserted into the bore. The anchoring groove means could also be helical threads, as described in U.S. Pat. No. 4,348,183, which also issued to the inventor of the present invention. In such latter case, a vertical channel is included for venting purposes. Accordingly, other types of anchoring arrangements could also be utilized in the present invention.

Laterally projecting on opposite sides of the cylindrical body portion 12, in diametrical opposed relationship, are a pair of projecting ribs 20, 22. Each of the ribs are elongated commencing at a substantially flat top surface 24 of the post 10, and extending longitudinally downwardly along a portion of the length of the body portion 12. Rib 22 extends lower than rib 20 to function as a pilot when inserting the post 10 into the bore. The combination of the cylindrical body portion 12 in conjunction with the laterally extending ribs 20, 22, provides an approximate oval shape which is more suitably contoured to the actual horizontal cross sectional shape of the canal in the prepared tooth stub, as will hereinafter be described.

The side outer edge 26, 28 of the ribs 20, 22 are downwardly tapered to be inclined relative to the longitudinal axis of the post 10, so that the upper portion of the dental post has the greatest oval shape, where the oval shape narrows progressively with the downward length of the post. This provides for a somewhat conical shape to the post 10, which again is more suitably contoured to the actual vertical cross sectional shape of the canal in the tooth stub, as will hereinafter be described. The lower end of the post 10 is shown chamfered at 30.

Figure 2:
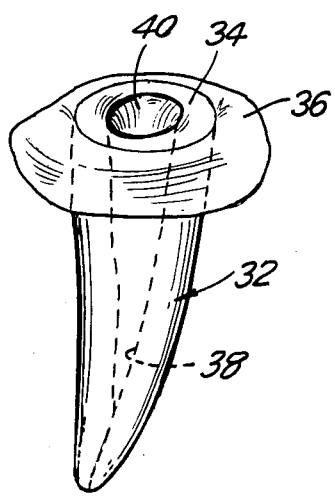
FIG. 2 is a perspective view showing a prepared tooth stub prior to the drilling of the contoured bore in its canal.

The contoured dental post 10 of the present invention will be inserted into a tooth stub 32, shown in FIG. 2, after the tooth stub 32 has been prepared. Initially, the tooth stub 32 has first been cut down to provide a prepared upper surface 34 situated within the gum area 36. The apical canal 38 provided in the tooth stub 32 has a substantially oval upper mouth portion 40 with a substantially conical vertical configuration. The upper mouth portion of the canal 38 is generally oval and flared at its upper edges.

A first step in the formation of the contoured bore in the tooth stub 32 is to drill into the canal 38 using a conventional dental drill 42 with an appropriate drill bit 44 to provide a central bore 46 in a manner well known in the art, drill bits of successively larger sizes may be utilized until the diameter and depth of the bore 46 is appropriate to receive the body portion 12 of the dental post 10.

As will be noted, however, the upper mouth portion 40 of the canal 38 is flared outwardly in a frustroconical shape, and substantially oval in cross sectional shape. As a result, even though the lower depth of the canal 38 is drilled into a circular shape defining the bore 46, the upper mouth portion 40 is wider than the bore 46, and outwardly flared, and accordingly, wider than the body portion 12 of the dental post 10 to be inserted therein. In the past, cement would have been used to fill in the space around the upper portion of the dental post of the prior art to pack the upper mouth portion 40 so as to tightly secure the prior art dental post. However, such cement would tend to loosen, and the prior art dental post and the restoration thereon would thus move with respect to the tooth stub, which is obviously not desirable, as stated above.

In the aforementioned parent application, the presence of the diametrically opposed redially projecting ribs served to accommodate the substantially oval cross sectional shape remaining at the upper portion of the predrilled bore. However, because the lateral edges of the ribs were longitudinally parallel to the axis of the post, and terminated in rounded lower corners, a considerable amount of the upper portion of the healthy dentition had to be drilled away to accommodate the longitudinal size of the ribs. By having the lateral edges of the ribs downwardly tapered, the vertical shape of the contoured dental post 10 of FIG. 1 more closely approximates the conical outwardly flared shape of the upper portion of the predrilled bore. As a result of the tapered ribs, less of the healthy dentition of the tooth stub is required to be contoured in order to closely accommodate the contoured post 10 of FIG. 1.

Figure 3:
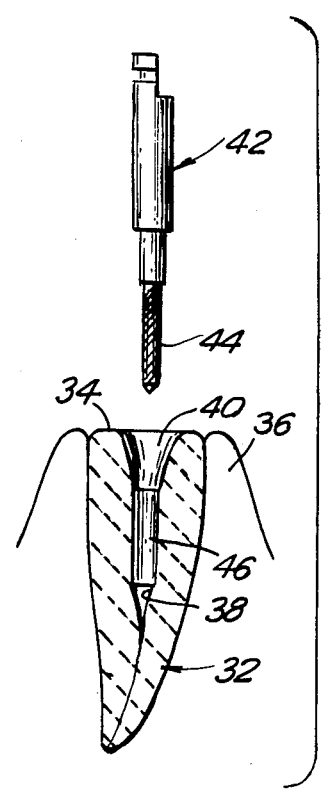
FIG. 3 is a cross sectional view through the tooth stub of FIG. 2, showing a first step in the formation of the contoured bore.

In order to properly contour the canal 38 of the tooth stub of FIG. 3, a dental drill jig can be utilized. Dental drill jigs were also described in the aforementioned parent application. However, those drill jigs were specifically designed for the projecting parallel ribs of the aforementioned parent application. With the modification of the lateral edges of the ribs, corresponding modification and structural change is required to the dental drill jig itself.

Figure 4:
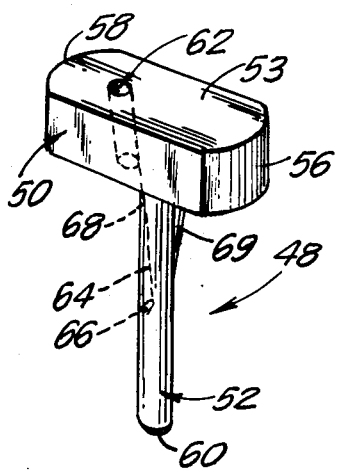
FIG. 4 is a perspective view of a dental drill jig for use in the formation of the contoured bore to receive the contoured dental post of FIG. 1.
Figure 5:
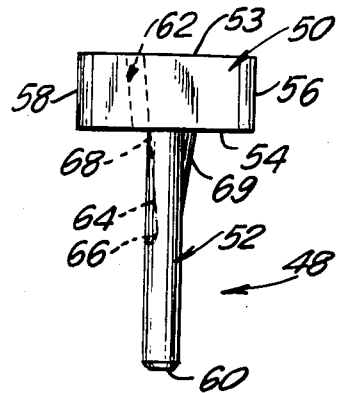
FIG. 5 is a side elevational view of the dental drill jig shown in FIG. 4.
Figure 6:
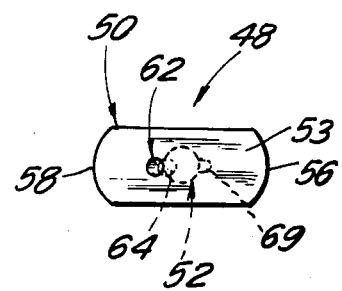
FIG. 6 is a top view of the dental drill jig shown in FIG. 4.

As shown in FIGS. 4, 5 and 6, there is provided a dental jig 48 which can be utilized to further drill out the canal and provide a suitably contoured bore shape. The dental jig 48 includes an upper head block 50 from which depends a central cylindrical shaft 52. The head block 50 is of uniform shape having upper and lower parallel flat surfaces 53, 54 with rounded interconnecting side edges 56, 58. The lower edge of the cylindrical shaft 52 can be chamfered at 60.

A single offset aperture 62 is angularly oriented and is inwardly directed toward the central shaft 52 as it passes through the head block 50. The aperture 62 extends downwardly in an inclined direction into the shaft 52, as shown by the dotted line 64. As the angled aperture 62 continues along the shaft 52, it provides a continuously greater penetration into the shaft 52 so that the lower end 66 of the aperture 62 in the shaft 52 is wider than the upper end 68 of the aperture 62 in the shaft 52. Since the aperture 62 is offset with respect to the shaft 52, the portion of the aperture 62 extending into the shaft 52 will be open along the shaft 52. The aperture 62 extends longitudinally along only a portion of the shaft 52 so that it terminates along the length of the shaft 52.

Projecting from the diametrically opposed side of the aperture 62 is a downwardly tapered fin 69 radially projecting from the shaft 52. The fin 69 extends along a portion of the length of the shaft 52 and terminates at a higher position on the shaft 52 than the lower end 66 of the aperture 62.

Figures 7, 8:
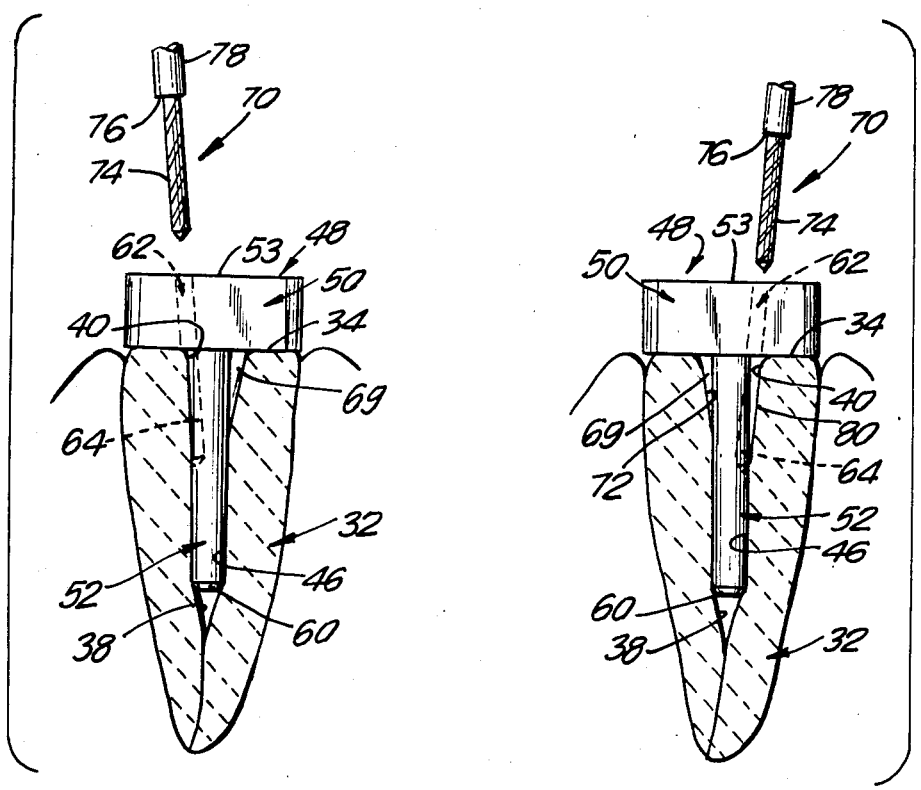
FIG. 7 shows a cross sectional view through the tooth stub similar to FIG. 3, showing the use of the dental drill jig of FIG. 4 in a second step in the formation of the contoured bore.
FIG. 8 is a cross sectional view similar to that shown in FIG. 7, showing a third step in the formation of the contoured bore.

As shown in FIG. 7, the drill jig 48 is mounted on the tooth stub 32 with the shaft 52 being inserted into the bore 46 and the head block 50 being placed on the upper surface 34 of the tooth stub 32. A drill 70 is positioned to be inserted into the angled aperture 62 so that the drill 70 can be rotated through the dentition 32 to form a tapered side wall 72 shown in FIG. 8. The fin 69 being shorter than the aperture 64 is accommodated in the natural tapered contour of the opposite side wall of the wider mouth portion 40 of the canal 38.

The drill 70 can be a selected size so that the length of the bit 74 corresponds to the entire depth of the aperture 62 including the aperture portion 64 extending into the shaft 52. In this manner, the shoulder 76 separating the drill bit 74 from its supporting shaft 78 will serve as a shoulder stop against the upper surface 53 of the head block 50 and form a natural stop to the depth of drilling into the dentition. It is noted, that the drill 70 has a smaller diameter than the drill 42, the diameter of the bit 74 of the drill 70 conforming in size to the size of the cross section of the ribs 20, 22.

The dental jig 48 is then removed and is flipped around so that the fin 69 is now positioned within the drilled arcuate side wall 72, and the aperture 62 is now adjacent the undrilled side wall 80. The same drill 70 is now used to form a second aperture in the opposite side wall 80 of the canal 38. The fin 69 serves as a stabilizing or positioning member to keep the jig 48 in place. This time, the drill 70 will only be partially inserted through the aperture 62 to form a shorter aperture than was previously drilled. Obviously, the shorter aperture could have been formed first before the longer aperture.

As a result, two opposing smaller apertures will be formed on either side of the larger center bore 46 to provide a contoured bore. The smaller apertures will be angled along the flared mouth portion 40 of the canal 38 corresponding to the natural flared taper of the canal 38. With one of these smaller apertures penetrating deeper than the other, the opposing smaller apertures will be suitable for receiving the opposing ribs 20, 22 provided on the opposite sides of the dental post 10. The dental post 10 will then comfortably fit into the contoured bore with less cement required to fill in disparity portions between the contoured bore and the dental post.

Figures 9, 10, 11:
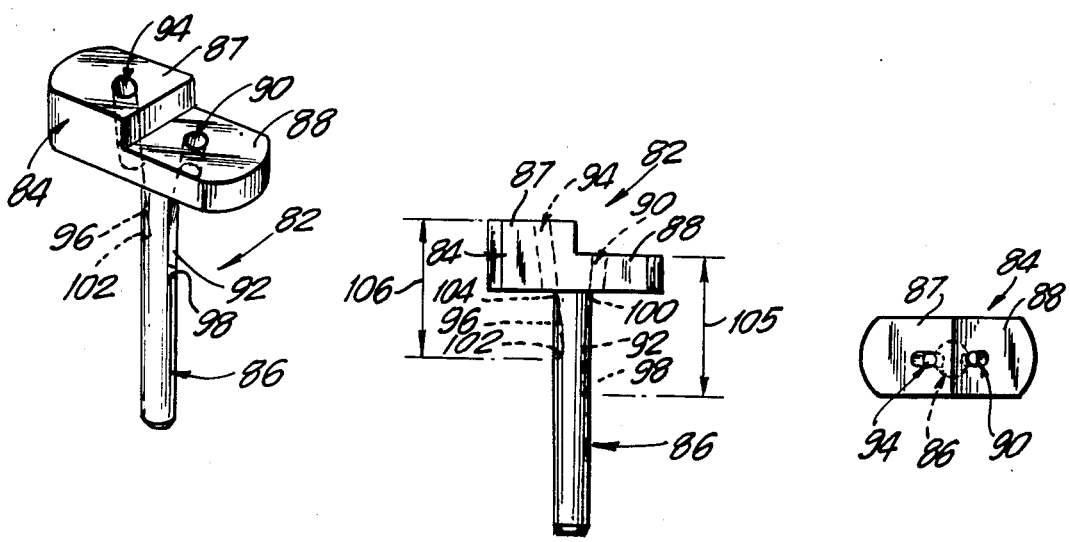
FIG. 9 is a perspective view of another dental drill jig for use in the formation of a similar type of contoured bore to receive the contoured dental post of FIG. 1.
FIG. 10 is a side elevational view of the dental drill jig shown in FIG. 9.
FIG. 11 is a top view of the dental drill jig shown in FIG. 9.

FIGS. 9, 10 and 11 show another type of dental jig 82 which can be used for the drilling of the canal 38 to suitably receive the contoured shaped dental post of FIG. 1.

The dental jig 82 includes an upper head block 84 from which depends a central cylindrical shaft 86. The head block 84 is stepped, having a thicker portion 87 and a thinner portion 88. A first angled aperture 90 extends through the thinner portion 88. At least a part 92 of the aperture 90 also continues into the shaft 86.

A second angled aperture 94 extends through the thicker portion 87 of the head block 84. At least a part 96 of this aperture 94 also extends into the shaft 86, and is diametrically opposed to the aperture part 92.

Both apertures 90 and 94 are angled and are inwardly directed towards the central shaft 86. The same angle of these apertures 90, 94 continues into the shaft 86 so that the penetration into the shaft 86 increases as the apertures move downward along the length of the shaft 86. In this manner, the bottom portion 98 of the aperture part 92 is deeper into the shaft 86 than its upper portion 100. Likewise, the lower end 102 of the aperture part 96 extends deeper into the shaft 86 than the upper end 104.

The entire lengths of both apertures 90 and 94 including the portions into the shaft 86 are actually equal to each other. Specifically, the distance 105 from the top surface of the thinner portion 88 to the bottom portion 98 of the aperture part 92 is the same as the distance 106 from the top surface of the thicker portion 87 to the lower end 102 of the aperture part 96. Thus, because of the varying stepped height arrangement of the head block 84, the aperture part 92 extends downwardly along the shaft 86 by an additional amount from that of the aperture part 96, this additional amount being the distance between the top surfaces of the thicker portion 87 and the thinner portion 88.

As shown in FIG. 12, the drill jig 82 is mounted on the tooth stub 32 with the shaft 86 being inserted in the bore 46 and the lower surface of the head block 84 being placed on the upper surface 34 of the tooth stub 32. The drill 70 is inserted into either one of the apertures 90, 94, such as the aperture 94 as indicated in FIG. 12, and is rotated until its shoulder portion 76, disposed between the bit 74 and the shaft 78, reaches the top surface of the thicker portion 87 of the head block 84. In this manner, a short aperture or bore 108 will be drilled into the canal wall 109 of the tooth stub 32 in communication with the bore 46, see FIGS. 13, 14. The bit 74 has a length equal to the entire length of each of the apertures 94 and 90, including these portions in the shaft 86.

With the same drill 70, a second aperture or bore 110 will now be drilled into the canal wall 111, also in communication with the bore 46, see FIG. 14. Because of the stepped arrangement of the head block 84, the same drill bit 74 can be utilized to drill the two bores 108 and 110, whereby the bore 110 will result in a deeper aperture in the tooth stub 32. As indicated in FIG. 13, the drill 70 is inserted into the other aperture 90, and the shoulder portion 76 of the drill 70 will abut the top surface of the thinner portion 88 to stop the depth of the drilling of the bore 110. Preferably, before drilling the bore 110, a pin 112 is inserted through aperture 94 into the bore 108 to maintain the drill jig 82 in a fixed position to insure the correct relationship between the bores 108 and 110. Obviously, the longer bore 110 could have been formed first before the shorter bore 108.

As shown in FIG. 14, after removal of the drill jig 82, a resulting contoured bore 114 is provided in the tooth stub 32, having a substantially cylindrical lower bore 46 with an upper aperture portion including a lateral angular bore 108 on one side, and a deeper lateral angular bore 110 on the opposing side. The contoured bore 114 approximates an oval shape at the upper aperture portion thereof, and is in close conformity to the actual oval cross sectional shape of the canal 38 of the tooth stub 32. Also, because the side bores 108, 110 are angled, they now provide a conical cross sectional which also closely approximates the conical shape of the actual shape of the canal 38. It is noted, that the contoured bore 114 shown in FIG. 14 is also obtained by using the above mentioned drill jig 48.

The dental post shown in FIG. 1 can now be inserted directly into the prepared contoured bore 114 in the tooth stub 32, as shown in FIG. 9, and can then be utilized in any of the well known dental techniques to form a dental core upon which the dental restoration can be built up in a known manner. As shown in FIG. 15, the contoured dental post 10 is now inserted into the contoured bore 114 in the tooth stub 32. The opposing ribs 20, 22 fit respectively into the angled lateral drilled bores 108, 110, and the body portion 12 fits into the predrilled bore 46 in the tooth stub 32. Appropriate cement 116 is placed into the contoured bore 114 to secure the contoured dental post 10 to the tooth stub 32. A dental core 122 is formed onto the upper projecting portion of the dental post 10 in any well known manner. The dental core 122 is secured onto the surface 34 of the tooth stub 32 by means of the cement 118. Appropriate dental material is then used to form a superstructure 120 which is disposed onto the core 122. Cement 126 can be used to retain the superstructure 120 in place on the core 122.

As can be noted in FIG. 15, the upper part of the outwardly flared ribs 20, 22 projects above the surface 34 of the tooth stub 32 and is embedded within the core 122. Because of the outwardly flared arrangement, the core 122 is fixedly secured onto the upper projecting portion of the dental post 10 for additional retention of the core 122 on the tooth stub 32. Accordingly, the tapering arrangement of the ribs 20, 22 not only provides a closer approximation to the actual canal 38 in the tooth stub, but also provides additional retention of the core 122 onto the dental post 10 by preventing rotation of the core 122 and also preventing the core 122 from being pulled vertically off the dental post 10.

Additional interlocking arrangements can be utilized to retain the dental post and core in secure relationship. Such interlocking relationships were described in the aforementioned parent application, where the use of the U-shaped clip, pin or other interlocking arrangements shown therein can also be applied with the dental post 10 shown in the present application.

Figure 16:
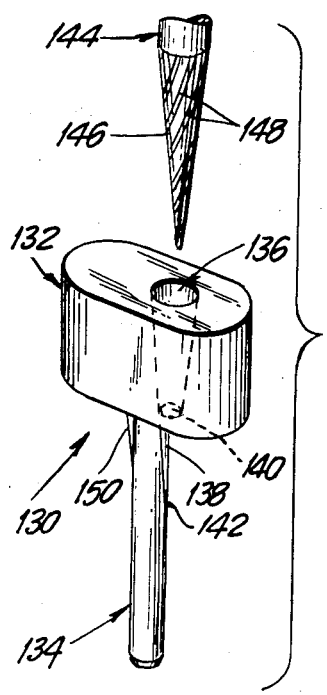
FIG. 16 is a perspective view of yet a further dental drill jig for use in the formation of another similar type of contoured bore to receive the contoured dental post of FIG. 1, showing its use in conjunction with a reamer for forming the contoured bore.
Figure 17:
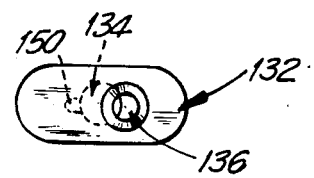
FIG. 17 is a top view of the dental drill jig shown in FIG. 16.
Figure 18:
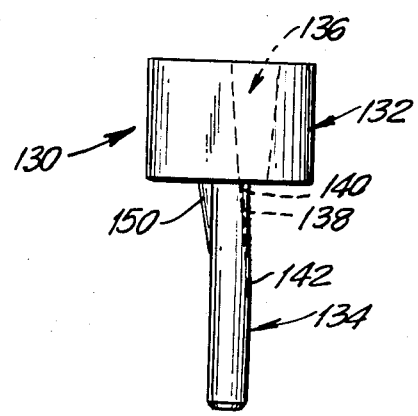
FIG. 18 is a side elevational view of the dental drill jig shown in FIG. 16.

Referring now to FIGS. 16, 17 and 18, another dental drill jig 130 is shown which can be used with a reamer instead of a drill. The dental jig 130 includes an upper head block 132 from which depends a central cylindrical shaft 134. An offset aperture 136 is formed into the head block 132 and continues downwardly into at least a portion of the shaft 134 to define an open aperture portion 138 along the shaft 134. Aperture 136 is downwardly conical in shape. The aperture portion 138 formed into the shaft 134 continues at the same angular relationship as the conical portion of the aperture 136 in the head block 132. Accordingly, there is a reduced amount of penetration in the cylindrical shaft 134 as the aperture portion 138 continues along the length of the shaft 134. There is therefore a wider penetration of the aperture at its upper end 140, which narrows and tapers to a slight penetration at the lower end 142.

A reamer 144 having a lower conical tip 146 can be used to ream out appropriate apertures in the tooth stub 32. The reamer tip 146 includes appropriate helical grooves 148 to facilitate reaming out of the apertures.

Radially projecting from the shaft 134 and diametrically opposed to the aperture portion 138 is a fin 150. The fin 150 is downwardly tapered as it proceeds along the length of the shaft 134. The fin 150 is shorter than the aperture portion 138 to terminate along the shaft spaced above the lower end 142 of the aperture portion 138.

Figure 19:
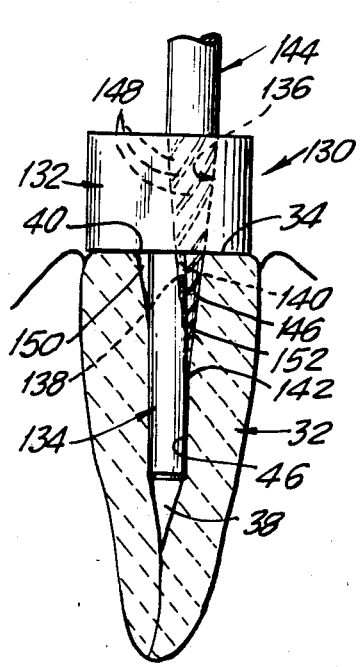
FIG. 19 shows a cross sectional view through the tooth stub similar to FIG. 3, showing the use of the dental drill jig of FIG. 16 and the reamer in a second step in the formation of the contoured bore.

As shown in FIG. 19, the drill jig 130 is mounted on the tooth stub 32 with the shaft 134 being inserted in the bore 46 and the lower surface of the head block 132 being placed on the upper surface 34 of the tooth stub 32. The reamer 144 is inserted into the conical offset aperture 136 and is rotated to ream out an aperture 152 alongside the bore 46 at an upper end of the canal 38. The fin 150 fits into the opposing side at the upper mouth 40 of the canal 38 and provides a stabilizing support during the reaming operation. As is noted in FIG. 19, the reamer 144 is inserted almost for its entire tip length in order that the aperture 152 should be of sufficient depth.

Figure 20:
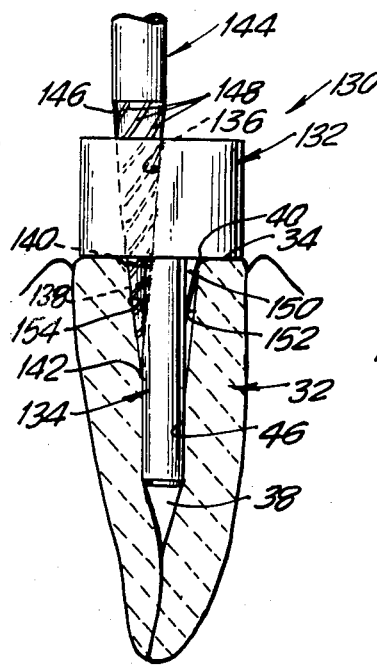
FIG. 20 is a view similar to that shown in FIG. 19, showing the use of the dental drill jig of FIG. 16 and the reamer in a third step in the formation of a contoured bore.

The reamer 144 is removed and the jig 130 is reinserted in a reverse direction. The fin 150 now enters the reamed aperture 152 and stabilizes the jig 130. As shown in FIG. 20, the reamer 144 is reinserted into the hole 136 and is again utilized to ream out an aperture 154 on the opposing side of the bore 46. However, the reamer 144 is not inserted to its full depth so that the reamed aperture 154 will penetrate into the dentition a shorter depth than the reamed aperture 152. Obviously, the shorter aperture 154 could have been formed first before the longer aperture 152.

Figure 21:
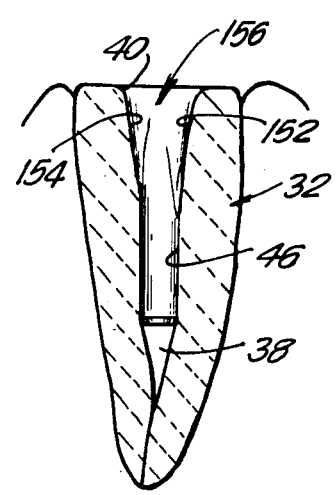
FIG. 21 is a cross sectional view through the tooth stub showing the contoured bore formed therein.

Upon removal of the reamer 144 and the jig 130, the tooth stub 32 will have a composite contoured bore 156, as shown in FIG. 21, including the dental bore 46 in communication with the lateral side apertures 152, 154 which conform in shape to the conical tapered configuration of the canal 38, similar to the contoured bore 114 shown in FIG. 14. The upper end will proximate the oval horizontal cross section at the mouth 40 of the canal 38. The dental post 10 of FIG. 1 can then be inserted into the tooth stub 32 with the lateral ribs 20, 22 being received respectively in the apertures 154 and 152. The dental post 10 can be secured in place, and the core and restoration built up as was previously described in connection with FIG. 15.

It should be appreciated, that although the dental jig 130 of FIGS. 16, 17 and 18 showed the use of a single conical aperture 136 in conjunction with a reamer 144, a suitable dental jig could also be prepared having an offset head arrangement with a pair of conical apertures similar to the jig 82 of FIG. 9. This would combine the embodiment shown in FIG. 16 with that of FIG. 9. In this case, there would not be provided any fin 150 projecting from the central shaft 134 since both sides of the shaft would include open apertures along a portion of the length thereof similar to the shaft 86 shown in FIG. 9. Accordingly, a showing of this latter case is not thought necessary, where the construction thereof would be obvious to one skilled in the art by an understanding of the above.

There has been disclosed heretofore the best embodiments of the invention presently contemplated. However, it is to be understood, that various changes and modifications may be made thereto without departing from the spirit of the present invention.

What is claimed is:

1. A dental post for retaining a dental restoration onto a prepared tooth stub having a canal with a bore drilled into the canal walls which have an approximate oval shape adjacent to an outer surface of the tooth stub, said dental post comprising:

an elongated cylindrical body portion having a substantially uniform circular cross section from a top end portion to a bottom end portion of said body portion;

rib means provided on an upper portion of said body portion for extending into the canal and for fitting the approximate oval shape of the canal in the tooth stub;

said rib means including a pair of diametrically opposed radially projecting ribs extending from said top end portion longitudinally along said upper portion of said body portion and being spaced from said bottom end portion;

both said ribs being continuously downwardly tapered from said top end portion of said body portion so that each of said ribs has its largest lateral cross section at said top end portion;

one of said ribs being longer than the other rib to provide pilot means for inserting said ribs into the bore; and said body portion including peripheral securing means for anchoring said body portion with cement within the bore in the tooth stub so that a part of said upper portion of said body portion extends above the tooth stub.

2. A dental post as in claim 1, wherein said peripheral securing means includes a plurality of externally spaced apart spiral grooves longitudinally disposed around said body portion for retaining a lower portion of said body portion within the cement in the bore, and also for providing a vent for said body portion when being inserted into the cement within the bore in the tooth stub.

3. A dental post for insertion within a bore formed in a canal of a prepared tooth stub, for retention of a dental restoration on the tooth stub, in combination with a drill jig for contouring the bore to receive said dental post;

said dental post comprising:

an elongated cylindrical portion;

anchoring means associated with said body portion for securing said post within the bore;

at least one rib radially projecting from said body portion and longitudinally extending along a portion of a length of said body portion for improving fitting relationship of said body portion within the canal;

said rib being downwardly tapered from a top portion of said body portion so that said rib has its largest lateral cross section at said top portion; and said drill jig comprising:

a head block and a depending central shaft extending from said head block for insertion into an initially drilled bore in the tooth stub;

at least one offset aperture having angled side walls passing through said head block and angularly extending along a portion of a length of said shaft; and said offset aperture being open along said shaft.

4. A dental post in combination with the drill jig as in claim 3, comprising only one offset aperture through said head block and continuing along said shaft, and further comprising a downwardly tapered fin radially projecting from said shaft in diametric opposition to said one aperture and extending longitudinally along at least a portion of said length of the shaft.

5. A dental post in combination with a drill jig as in claim 4, wherein said fin has a length less than the length of said portion of said one aperture along said shaft.

6. A dental post in combination with a drill jig as in claim 4, wherein said one offset aperture is inwardly angled through said head block toward said shaft and maintains said angle along said shaft thereby providing continuously deeper penetration into said shaft as said one offset aperture extends downwardly along said portion of said shaft.

7. A dental post in combination with a drill jig as in claim 4, wherein said one offset aperture is a downwardly tapered conical hole through said head block, and longitudinally continues along said shaft thereby providing a reduced penetration into said shaft as said one offset aperture extends downwardly along said portion of said shaft.

8. A dental post in combination with a drill jig as in claim 3, and comprising two offset apertures both inwardly angled towards said central shaft passing through said head block and extending into diametrically opposed portions of said shaft, both apertures providing continuing deeper penetration into said shaft as said apertures extend downwardly along said shaft.

9. A dental drill jig for contouring a bore in a tooth stub to accommodate a dental post for retaining a dental restoration, said drill jig comprising:
   a head block;
   a depending shaft extending from said head block for insertion into a predrilled center bore in the tooth stub; and
   an offset aperture in said head block having angled walls passing through said head block and angularly extending along a portion of a length of said shaft, said offset aperture being open along said shaft.

10. A dental drill jig as in claim 9, and further comprising a downwardly tapered fin radially projecting from said shaft in diametric opposition to said aperture, said fin extending longitudinally along at least a portion of said length of said shaft.

11. A dental drill jig as in claim 10, wherein said fin has a length less than the length of said portion of said aperture along said shaft.

12. A dental drill jig as in claim 10, wherein said offset aperture is inwardly angled through said head block toward said shaft and maintains its angle along said shaft providing continuing deeper penetration into said shaft as said aperture extends downwardly along said portion of said shaft.

13. A dental drill jig as in claim 10, wherein said offset aperture is a downwardly tapered conical hole through said head block and longitudinally continues along said shaft thereby providing a reduced penetration into said shaft as said aperture extends downwardly said portion of said shaft.

14. A dental drill jig as in claim 9, comprising two offset apertures inwardly angled toward said shaft, said two apertures passing through said head block and extending into diametrically opposed portions of said shaft, both said apertures providing continuing deeper penetration into said shaft as said two apertures extend downwardly along said shaft.

15. A dental drill jig as in claim 14, wherein one aperture has a shorter length along said shaft than the other aperture.

16. A dental drill jig as in claim 14, wherein a top portion of said head block is stepped to provide a thinner and thicker portion, said thinner portion of said head block being provided with one of said offset apertures and said thicker portion of said head block being provided with the other offset aperture.

17. A dental drill jig as in claim 16, wherein entire length of each of said offset apertures are equal to each other.

* * * * *